United States Patent [19]

Roman et al.

[11] 4,211,792
[45] Jul. 8, 1980

[54] OXYIMINO-SUBSTITUTED (1R,TRANS)-CYCLOPROPANECARBOXYLATE PESTICIDES

[75] Inventors: Steven A. Roman, Oakdale; Samuel B. Soloway, Modesto, both of Calif.

[73] Assignee: Shell Oil Company, Houston, Tex.

[21] Appl. No.: 13,778

[22] Filed: Feb. 21, 1979

Related U.S. Application Data

[63] Continuation-in-part of Ser. No. 911,743, Jun. 2, 1978, abandoned.

[51] Int. Cl.² .............. A01N 9/24; C07C 131/02; C07C 131/04
[52] U.S. Cl. .............. 424/304; 260/326 N; 260/347.2; 260/347.4; 260/430; 260/465 D; 260/501.11; 260/544 L; 424/274; 424/285; 424/305; 424/309; 542/421; 560/35; 560/118; 560/124; 562/440; 562/500; 562/506
[58] Field of Search ............. 260/326 N, 347.2, 347.4, 260/430, 465 D, 501.11, 544 L; 424/274, 285, 304, 305, 309; 542/421; 560/35, 118, 124; 562/440, 500, 506

[56] References Cited

U.S. PATENT DOCUMENTS

| 3,922,269 | 11/1975 | Elliott et al. | 260/347.4 |
| 4,024,163 | 5/1977 | Elliott et al. | 260/347.4 |

OTHER PUBLICATIONS

Elliott et al., J. C. S. Perkin I, (1974) pp. 2470–2474.

*Primary Examiner*—Richard Raymond

[57] ABSTRACT

(1R,trans)-cyclopropane compounds, substantially free of other stereoisomers, and having the formula

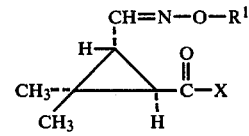

wherein
X is chlorine, bromine or OR in which
R is hydrogen, a salt-forming cation, an alkyl group or residues of certain other alcohols; and
R¹ is certain optionally halogenated hydrocarbyl groups, are highly active pesticides or intermediates therefore.

10 Claims, No Drawings dd
OXYIMINO-SUBSTITUTED (1R,TRANS)-CYCLOPROPANECARBOXYLATE PESTICIDES

CROSS-REFERENCE TO RELATED APPLICATIONS

This application is a continuation-in-part of Ser. No. 911,743, filed June 2, 1978, now abandoned.

BACKGROUND OF THE INVENTION

1. Field of the Invention

This invention is directed to new oxyimino-substituted compounds, their use as pesticides, to pesticidal formulations containing these new compounds and to certain novel intermediates.

2. Description of the Prior Art

U.S. Pat. No. 3,922,269 describes a class of 2,2-dimethyl-3-(oxyiminomethyl)cyclopropanecarboxylic acid esters useful as insecticides. In the case of such esters of α-substituted asymmetric alcohols, three asymmetric centers and one oxime double bond are present and therefore a total of sixteen theoretical stereoisomers are possible. Eight theoretical stereoisomers are possible when there is no asymmetric center in the alcohol moiety. The above-mentioned patent states that esters, in which the two hydrogen atoms on the cyclopropane ring are in the absolute stereochemical relationship equivalent to that in (+)-trans-chrusanthemic acid, tend to be among the most insecticidally active of the various isomers and are preferred for that reason. Indeed, only a very few (1R,trans)-cyclopropanecarboxylate oximes were apparently prepared and tested, and form the basis of the working examples. In all of these compounds, the oxime function contains a $C_{1-3}$ alkyl group, usually a methyl group.

SUMMARY OF THE INVENTION

It has now been found that certain oxyimino-substituted cyclopropanecarboxylates derived from the (1R,trans)-form of 2,2-dimethyl-3-formyl-cyclopropanecarboxylic acidin which the oxime function is other than methyl, ethyl or n-propyl, are useful pesticides (insecticides and acaricides) and exhibit high knockdown characteristics.

Therefore, this invention is directed to new (1R,trans)-cyclopropane compounds, substantially free of other stereoisomers, and having the formula wherein $R^1$ represents a branched-chain alkyl group containing from 3 to 5 carbon atoms; an alkyl group containing from 1 to 10 carbon atoms substituted by one or more halogen atoms, a (cycloalkyl)alkyl group containing from 3 to 7 ring carbon atoms, a total of from 4 to 9 carbon atoms and optionally ring-substituted by one or more halogen atoms, a cycloalkyl group containing from 3 to 7 ring carbon atoms, an alkenyl group containing from 3 to 4 carbon atoms substituted by one or more halogen atoms or alkynyl group containing from 3 to 4 carbon atoms or an aryl group containing from 6 to 12 carbon atoms or an aralkyl group containing from 7 to 10 carbon atoms, each optionally ring-substituted by one or more halogen atoms; X is chlorine, bromine or OR in which R represents a hydrogen atom, a salt-forming cation, an alkyl group containing from 1 to 20 carbon atoms or a group of the formula wherein Y represents hydrogen or an alkyl, alkenyl or alkynyl group or an aryl or furyl group which is unsubstituted or substituted in the ring by one or more alkyl, alkenyl, alkoxy or halogeno groups, $R^7$ and $R^8$, which may be the same or different, each represent hydrogen or an alkyl or alkenyl group, $R^9$ represents hydrogen or a methyl group, $R^{10}$ and $R^{11}$ represent hydrogen or an alkyl group, $R^{12}$ represents an organic radical having carbon-carbon unsaturation in a position α to the $CH_2$ group to which $R^{12}$ is attached, A/S indicates an aromatic ring or a dihydro or tetrahydro analogue thereof, $X^1$, $X^2$, $X^3$ and $X^4$, which may be the same or different, each represents hydrogen, halogen or a methyl group, D represents H, —CN, —C≡CH or

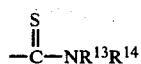

in which $R^{13}$ and $R^{14}$ may be the same or different, each represent a hydrogen atom or an alkyl group containing from 1 to 10 carbon atoms, Z represents —CH$_2$—, —O—, —CO— or —S—; $Z^1$ and $Z^2$, which may be the same or different, each represent halogen or an alkyl group containing 1 to 4 carbon atoms and n is 0, 1 or 2, with the proviso that when D is —CN, —C≡CH or

then the alcohol moiety is in the R,S-racemic or in the S-optical configuration.

In the above-formulas, suitable halogen atoms substituents are chlorine, fluorine or bromine.

Since the biological activity of various optical or geometric isomers and diastereoisomer pairs within the (1R,trans) esters of the invention may differ somewhat, it may be desirable to use a more active optical and/or geometric isomer or diastereoisomer pair of the invention substantially free of the other isomers or pair.

The oxime substituent group of the compounds of the invention gives rise to geometric isomerism by virtue of the presence of an asymmetrically substituted double bond. These isomers are usually described as follows:

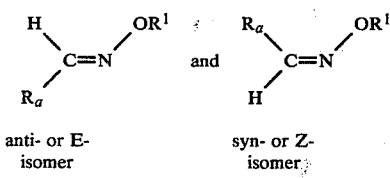

anti- or E-isomer    syn- or Z-isomer

It should be noted that compounds wherein $R^1$ is haloalkyl, (cycloalkyl)alkyl optionally substituted by halogen, haloalkenyl, alkynyl, aryl optionally substituted by halogen, or aralkyl optionally substituted by halogen are also novel not only in the (1R,trans) but also in the racemic form as for example α-cyano-3-phenoxybenzyl-2,2-dimethyl-3-((cyclopropylmethoxyimino)methyl)cyclopropanecarboxylate, 3-phenoxybenzyl-2,2-dimethyl-3-((cyclopropylmethoxyimino)methyl)cyclopropanecarboxylate and α-cyano-3-phenoxybenzyl-2,2-dimethyl-3-((cyclopentoxyimino)methyl)cyclopropanecarboxylate.

The (1R,trans) esters of the present invention wherein R represents a group of formula I, II, III, IV, V, VI or VII above are pesticidally active.

The other oxyimino-substituted (1R,trns) cyclopropane compounds described above in which X is chlorine, bromine or OR in which R represents a hydrogen atom, a salt-forming cation or an alkyl group are useful intermediates for the production of the pesticidal esters.

When the (1R,trans) ester is one formally derivable from a furylmethyl alcohol, it is preferred that the furylmethyl alcohol be a 3-furylmethyl alcohol as described and claimed in U.S. Pat. No. 3,466,304.

In the furylmethyl alcohols (R is formula I), and particularly in the 3-furylmethyl alcohols, it is preferred that $R^7$ and $R^8$ each represent hydrogen or groups containing up to 4 carbon atoms, particularly a methyl group and the Y represents a phenyl group which is unsubstituted or substituted in the ring by a group containing up to 4 carbon atoms, e.g., methyl or methoxy, or by chlorine and Z is CH$_2$ and D is H. Analogues of these compounds where Z is O, S or CO and D is CN or C≡CH are also of interest. Further compounds of interest are those where Y represents a hydrogen atom, an alkyl group containing up to 4 carbon atoms, an alkenyl group containing up to 4 carbon atoms, e.g., vinyl, an alkadienyl group containing up to 4 carbon atoms or an alkynyl group, e.g., propargyl, or a furyl group.

Specific alcohols of this category, from which the (1R,trans) esters of the invention are formally derivable, include 5-benzyl-3-furylmethyl alcohol, 5-benzyl-2-methyl-3-furylmethyl alcohol, 4-benzyl-5-methyl-2-furylmethyl alcohol, 5-(p-methoxybenzyl)-3-furylmethyl alcohol, 2,4,5-trimethyl-3-furylmethyl alcohol and 4,5-dimethyl-2-furylmethyl alcohol, 5-phenoxy- and 5-benzoyl-3-furylmethyl alcohol and α-cyano substituted 5-benyl-, 5-benzoyl- or 5-phenoxy-3-furylmethyl alcohol.

The cyclopentenolones from which the (1R,trans) esters of the invention are formally derivable are those unsubstituted in the 3-position or those substituted in the 3-position by a methyl group ($R^9$=H or CH$_3$).

The cyclopentenolones (R is formula II) unsubstituted in the 3-position are described and claimed in U.S. Pat. No. 3,720,703.

Some of these alcohols are the 3-desmethyl analogues of the alcohols from which the naturally occurring pyrethrins are derived. In the present invention, it is preferred that $R^{10}$ and $R^{11}$ each represent hydrogen, methyl or ethyl and $R^{12}$ represents an aryl group such as a phenyl group or a phenyl group substituted by a halogeno or alkyl or alkoxy substituent of 1 to 4 carbon atoms, for example tolyl, xylyl, p-chlorophenyl or p-methoxyphenyl. $R^{12}$ may also represent a 2- or 3-furyl group or an alkenyl group such as vinyl, 1-propenyl or 1,3-butadienyl group.

When the (1R,trans) esters of the invention are formally derivable from the cyclopentenolones which are substituted in the 3-position by the methyl group ($R^9$=methyl), the (1R,trans) esters may be derived from allethrolone ($R^{10}=R^{11}=H$, $R^{12}=$vinyl), pyrethrolone ($R^{10}=R^{11}=H$, $R^{12}=$1,3-butadienyl), cinerolone ($R^{10}=R^{11}=H$, $R^{12}=$1-propenyl), jasmolone ($R^{10}=R^{11}=H$, $R^{12}=$1-butenyl), or furethrolone ($R^{10}=R^{11}=H$, $R^{12}=$2-furyl).

When the (1R,trans) esters of the invention are phthalimidomethyl esters where R is of formula III, they may be phthalimido, dihydrophthalimido or tetrahydrophthalimidomethyl esters where the phthalimido, dihydrophthalimido or tetrahydrophthalimido residue (R is formula III) is one described in British Pat. Nos. 985,006, 1,052,119 or 1,058,309. 3,4,5,6-Tetrahydrophthalimidomethyl esters are of particular interest.

When the (1R,trans) esters of the invention are those where R is of formula IV, it is preferred that they be 3-benzylbenzyl esters, 3-benzoylbenzyl esters, or 3-phenoxybenzyl esters, although each of the rings may be substituted by up to 3 chloro and/or methyl groups. Other esters of particular interest where R is of formula IV are those where Z represents O or CH$_2$ and D represents CN or C≡CN e.g., esters of α-cyano or α-ethynyl substituted 3-phenoxy-, 3-benzyl or 3-benzyloxybenzyl alcohol. Such alcohols are described in U.S. Pat. Nos. 3,666,789, 3,835,176 and 3,862,174.

Variations in activity, of course, depend on the individual combinations of R and $R^1$ and are somewhat depending on the susceptibility of an individual pest to certain structural subtleties in the various combinations of R and $R^1$.

Typical examples of species within the scope of the invention are

α-ethynyl-5-benzyl-3-furylmethyl (1R,trans)-2,2-dimethyl-3-((sec-butoxyimino)methyl)-cyclopropanecarboxylate α-cyano-3-phenoxybenzyl (1R,trans)-2,2-dimethyl-3-((propargyloxyimino)methyl)-cyclopropanecarboxylate 3-phenoxybenzyl (1R,trans)-2,2-dimethyl-3-((isobutoxyimino) methyl)-cyclopropanecarboxylate α-thiocarbamoyl-3-benzylbenzyl (1R,trans)-2,2-dimethyl-3-(trifluoromethoxyimino)methyl)-cyclopropanecarboxylate 3-phenoxybenzyl (1R,trans)-2,2-dimethyl-3-((p-chlorophenoxyimino)methyl)cyclopropanecarboxylate 3-phenoxybenzyl (1R,trans)-2,2-dimethyl-3-((cyclopentoxyimino)methyl)-cyclopropanecarboxylate 3-phenoxybenzyl (1R,trans)-2,2-dimethyl-3-((2-chloroethoxyimino)methyl)-cyclopropanecarboxylate α-cyano-3-phenoxybenzyl (1R,trans)-2,2-dimethyl-3-((1-cyclopropyl)ethoxyimino)methyl)-cyclopropanecarboxylate α-ethynyl-3-phenoxybenzyl (1R,trans)-2,2-dimethyl-3-((phenethoxyimino)methyl)-cyclopropanecarboxylate 3-(phenylthio)benzyl (1R,trans)-2,2-dimethyl-3-((neopentoxyimino)methyl-cyclopropanecarboxylate 3-(p-fluorophenoxy)benzyl (1R,trans)-2,2-dimethyl-3-(cyclopropylmethoxyimino)methyl)-cyclopropanecarboxylate Because of their pesticidal utility in agricultural and domestic situations, preferred compounds of the invention (subject to the same provisions stated above) are those wherein R is 5-benzyl-3-furylmethyl, α-cyano-3-phenoxybenzyl, 3-phenoxyenzyl or α-ethynyl-3-phenoxyenzyl and $R^1$ is a branched-chain alkyl group containing from 3 to 5 carbon atoms, a (cycloalkyl)alkyl group containing from 3 to 6 ring carbon atoms, a total of from 4 to 8 carbon atoms and optionally ring-substituted by from 1 to 4 chlorine, fluorine and/or bromine atoms, a cycloalkyl group containing from 3 to 6 ring carbon atoms, an alkenyl group containing from 3 to 4 carbon atoms substituted by one or two chlorine, fluorine and/or bromine atoms or an alkynyl group containing from 3 to 4 carbon atoms, an aryl group containing from 6 to 12 carbon atoms or an aralkyl group containing from 7 to 10 carbon atoms.

In the pesticidal (1R,trans) esters of the invention, $R^1$ preferably represents a branched-chain alkyl group containing 3 to 6 carbon atoms, such as isopropyl, sec-butyl, isobutyl, tert-butyl, isoamyl, sec-amyl, tert-amyl, neopentyl and the like, a (cycloalkyl)alkyl group containing from 3 to 6 ring carbon atoms and a total of from 4 to 8 carbon atoms, such as cyclopropylmethyl, 1-(cyclopropyl)ethyl, cyclohexylmethyl and the like, a cycloalkyl group containing 3 to 6 ring carbon atoms, such as cyclopropyl, cyclobutyl, cyclopentyl or cyclohexyl and the like, an alkenyl or alkynyl group containing 3 to 4 carbon atoms such as propargyl and the like, an aryl group containing from 6 to 10 carbon atoms such as phenyl or an aralkyl group containing from 7 to 10 carbon atoms, such as benzyl, phenethyl or the like.

Preferred because of their pesticidal properties are those (1R,trans) esters wherein $R^1$ is a branched-chain alkyl group containing from 3 to 5 carbon atoms, a (cycloalkyl)alkyl or cycloalkyl group containing 4 or 5 carbon atoms, phenyl or enzyl. Particularly suitable are those compounds wherein $R^1$ is a branched-chain alkyl, (cyclopropyl)alkyl or cycloalkyl group containing 4 or 5 carbon atoms, particularly neopentyl, isobutyl, tert-butyl, cyclopentyl, (cyclopropyl)methyl or cyclobutylmethyl.

Because of their pesticidal activity and ease of preparation, one preferred subclass of the invention are those esters wherein R is derived from 3-phenoxybenzyl alcohol. Examples of some highly active compounds of this subclass of the invention are:

3-phenoxybenzyl (1R,trans)-2,2-dimethyl-3-((cyclopropylmethoxyimino)methyl)cyclopropanecarboxylate and 3-phenoxybenzyl (1R,trans)-2,2-dimethyl-3-((isobutoxyimino)methyl)cyclopropanecarboxylate.

Because of their pesticidal activity, another peferred subclass of the invention are those (1R,trans) esters derived from α-cyano-3-phenoxybenzyl alcohol, particularly in the S-optical configuration. In fact, the (1R,trans) esters wherein the alcohol substituent is in the R-α-cyano-3-phenoxybenzyl alcohol form are without practical insecticidal utility. Thus, one preferred embodiment of the invention is directed to those (1R,trans) esters derived from α-cyano-3-phenoxybenzyl alcohol in which such alcohol is in a racemic or, alternatively, in a S-optical configuration. Examples of some highly active compounds of this subclass of the invention are the following compounds wherein R is derived from α-cyano-3-phenoxybenzyl alcohol and $R^1$ is an alkyl, (cycloalkyl)alkyl or cycloalkyl group contaiing 4 to 5 carbon atoms:

α-cyano-3-phenoxyenzyl (1R,trans)-2,2-dimethyl-3-((cyclopropylmethoxyimino)methyl)cyclopropanecarboxylate, α-cyano-3-phenoxybenzyl (1R,trans(-2,2-dimethyl-3-((sec-butoxyimino)methyl)cyclopropanecarboxylate, α-cyano-3-phenoxybenzyl (1R,trans)-2,2-dimethyl-3-((isobutoxyimino)methyl)cyclopropanecarboxylate, α-cyano-3-phenoxybenzyl (1R,trans)-2,2-dimethyl-3-((tert-butoxyimino)methyl)cyclopropanecarboxylate, α-cyano-3-phenoxybenzyl (1R,trans)-2,2-dimethyl-3-((neopentoxyimino)methyl)cyclopropanecarboxylate, and α-cyano-3-phenoxybenzyl (1R,trans)-2,2-dimethyl-3-((cyclopentoxyimino)methyl)cyclopropanecarboxylate which compounds are pesticidally active when the alcohol moiety is present in the R,S-racemic or S- optically active form, and the oxime substituent is in the Z-isomer form or in a mixture of the E- and Z-isomer forms.

A particularly preferred subclass of the invention are those (1R,trans) esters derived from the S-α-cyano-3-phenoxybenzyl alcohol and wherein the oxime substituent is the Z-isomer form.

Because of their useful pesticidal properties, one preferred class of (1R,trans) esters of the invention comprise those compounds wherein $R^1$ is (cycloalkyl)alkyl and R is one of the groups of formulas I—VII. Particularly preferred are (1R,trans) esters wherein $R^1$ is cyclopropylmethyl, and R is 3-phenoxybenzyl or α-cyano-3- phenoxybenzyl or individual diastereoisomers of such (1R,trans) esters.

When R is a salt-forming cation, it is selected from alkali metals, alkaline earth metals, aluminum, heavy metals, such as copper, silver, nickel and the like, ammonia or a tetrahydrocarbylammonium compound in which the total number of carbon atoms in the hydrocarbyl groups is between 4 and 70 carbon atoms. The hydrocarbyl groups can be alkyl, aryl, aralkyl and the like. Preferably, the hydrocarbyl groups are selected from alkyl groups containing from 1 to 10 carbon atoms and aralkyl groups containing from 7 to 10 carbon atoms.

When R is an alkyl group, it contains from 1 to 20 carbon atoms, and preferably from 1 to 6 carbon atoms, for example, methyl, ethyl, n-propyl, tert-butyl and the like.

The pesticidal (1R,trans) esters of the present invention may be prepared by esterification involving the reaction of an alcohol or derivative thereof of formula RQ e.g., of formula VIII or IX, and a (1R,trans)-cyclopropane carboxylic acid or derivative thereof formula X,

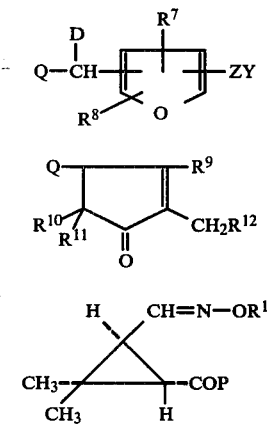

where Q and COP are functional groups or atoms which will react to form an ester linkage and R, R$^1$, R$^7$, R$^8$, R$^9$, R$^{10}$, R$^{11}$, R$^{12}$, D, Z and Y are as defined above.

It is usually convenient in practice either to treat the acid or acid halide with the alcohol (COP=COOH or CO-halide and Q=OH) or to treat a halogeno compound (Q=halogen) with a salt of the carboxylic acid (COP=COO—M where M is, for example, a silver or triethylammonium cation).

Transesterification is not always practical and, it is useful to prepare the intermediate (1R,trans) alkyl ester as a tert-butyl ester (R=tert-butyl) which can be selectively converted (under acid conditions) to give the free acid which can, after conversion to the acid halide, be esterified to a pesticidal (1R,trans)ester.

Suitable routes to the (1R,trans) esters in which D is

are similar to those described in Belgian Pat. No. 839,360. One route involves treating the corresponding nitrile (D is —CN) with hydrogen sulfide in the presence of a basic catalyst, preferably in the presence of a solvent. Useful solvents are lower alkanols, pyridine, or preferably a dipolar aprotic solvent, such as dimethylformamide or hexamethylphosphoramide. The catalyst is preferably a strong nitrogeneous base, particularly a tertiary amine such as triethylamine, trimethylamine, or the like, or an alkanolamine, such as triethanolamine and the like. The reaction can be carried out at room temperature. It is desirable that the reaction solution be saturated with hydrogen sulfide.

The (1R,trans) alkyl esters of the present invention can also be prepared by treating an ester of (1R,trans)-caronaldehyde of formula

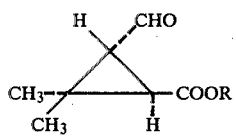

where R is an alkyl group, with hydroxylamine or an O-substituted hydroxylamine of formula R$^1$ONH$_2$ where R$^1$ is as defined above, and in the case where R$^1$ represents hydrogen, subsequently hydrocarbylating the resulting oxime, if desired, with an alkyl (or alkenyl) halide or the like, to give an alkoxime (or alkenyloxime), etc. Oxime formation can take place by treating substantially equimolar amounts of aldehyde and hydroxylamine or hydrocarbyloxyamine in a polar solvent such as an alkanol, e.g., ethanol or dioxane. When the aldehyde is converted into the oxime by reaction with hydroxylamine and it is desired to convert the resulting oxime into an alkylated or alkenylated derivative or the like, this reaction may be carried out by procedures customarily used for the alkylation of phenols. Thus, the oxime may be treated in a polar solvent, such as ethanol, with an alkyl halide, typically the bromide, in the presence of a hydrogen halide acceptor and the mixture heated until reaction is complete.

Oxime formation is normally carried out using an acid addition salt of hydroxylamine or the hydrocarbyloxyamine, e.g., the hydrochloride. In the cases where it is desired to prepare a (1R,trans) compound where R$^1$ represents methyl, the availability of methoxylamine hydrochloride makes it generally more convient to carry out the reaction in one step using methoxylamine hydrochloride, but when compounds are required where R$^1$ represents a larger group, it is usually more convenient to form the oxime first and subsequently to hydrocarbylate the oxime. Several analogs can not be prepared by alkylation of the =N—OH; eg., neopentyl and t-butyl.

Alcohols and halides of formula VIII are described and claimed in U.S. Pat. No. 3,720,703.

Alcohols of formula RQ where R is a group of formula IV may be prepared by reduction of the corresponding acids or esters or aldehyde e.g., with hydride, or by conversion of the corresponding halide to an ester, e.g., by reaction with sodium acetate, followed by hydrolysis of the ester, or by reaction of formaldehyde with a Grignard reagent derived from the corresponding halide. The halides of formula RQ where R is a group of formula IV can be prepared by halomethylation of the compound

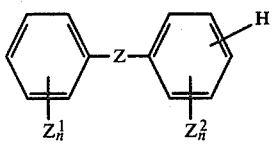

or side chain halogenation of

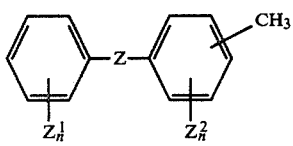

An isomer mixture of the (1R,trans) esters of the invention are readily separated into the individual diastereoisomers using known procedures, as for example, by preparative scale liquid chromatography. One such chromatographic system which can be employed has the following characteristics:
Column—porisil polar bonded phase, 9.2×250 mm
Mobile Phase—8% v/v diethyl ether in n-hexane
Flow Rate—2.5 ml/min
Detection—$UV_{254}$ at 2.0 AUFS
Injection—typically 500 ml of a 20 mg/ml solution in the mobile phase.
Such a procedure readily yields the single diastereoisomers in greater than 90% purity (as determined by NMR analysis). In the case of esters of α-substituted alchols four diastereoisomers are obtained.

The invention includes, within its scope, pesticidal compositions comprising a pesticidally acceptable adjuvant—that is, at least one carrier or a surface-active agent—and, as active ingredient, at least one pesticidally active (1R,trans) ester of this invention. Likewise, the invention includes also a method of combatting insect, acarine or other arthropod pests at a locus which comprises applying to the pests or to the locus a pesticidally effective amount of at least one compound of the invention.

With respect to the spectrum of pesticidal activity, the compounds of this invention exhibit a selective or non-selective activity on such orders as Coleoptera, Lepidoptera (especially larvae), Diptera, Orthopttera, Hemiptera, Homoptera and Acarina depending upon a specific combination of acid and an alcohol according to the present invention. The compositions according to the present invention are very useful for controlling disease carrying insects such as mosquitoes, flies and cockroaches, grain insects such as rice weevil (*Sitophilus oryzae*) and mites as well as agricultural noxious insects such as plant-hoppers, green rice leafhopper (*Nephotettix bipuntatus cinticeps* Uhler), diamond-back moths (*Plutella maculipennis* Curtis), imported cabbage worm (*Pieris rapae* Linne), rice stem borers (*Chilo suppressalis* Walker), corn earworm larvae (*Heliothis zea* Boddie), aphids, tortrixes, leaf-miners and the like.

The (R,trans) esters are used for harvested crops, horticultural application, forests, cultures in green house, and packaging materials for foodstuffs, household applications and as ectoparasiticides.

The term "carrier" as used herein means a material, that may be inorganic or organic and of synthetic or ntural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous erths; magnesium silicates, for example, talcs; magnesium aluminum silicates, for example, attapulgites and vermiculities; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen; waxes such as beeswax, paraffin wax, and chlorinated mineral waxes; degradable organic solids, such as ground corn cobs and walnut shells; and solid fertilizers, for example superphosphates.

Suitable liquid carriers include solvents for the compounds of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchloroethylene, trichloroethane, including liquified normally vaporous gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acids salts of low molecular weight, mino-, di- and trialkyl-amine; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations are also contemplated, as are bait formulations. Wettable powders are usually compounded to contain 24, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by extrusion of plastics, agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, cosolvent, 10–50%W/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%wt toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

Particularly useful compositions can be obtained by using a mixture of two or more kinds of the present compounds, or by the use of synergists, such as those known for use with the general class of "pyrethroid" compounds, especially α-[2-(2-butoxyethoxy)ethoxy]-4,5-methylenedioxy-2-propyltoluene also known as piperonyl butoxide, 1,2-methylenedioxy-4-[2-(octylsulfinyl)propyl]benzene, 4-(3,4-methylenedioxyphenyl)-5-methyl-1,3-dioxane also known as safroxane, N-(2-ethyhexyl)bicyclo-[2,2,1]hept-5-ene-2,3-dicarboximide, octachlorodipropyl ether, isobornyl thiocyanoacetate, and other synergists used for allethrin and pyrethrin. Useful compositions can be prepared with other biological chemicals including other cyclopropanecarboxylates, organic phosphate type insecticides and carbamate type insecticides.

The compositions of the invention are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of toxicants of this invention at the locus to be protected—i.e. the applied dosage—is of the order or 0.01% to 0.5% based on the total weight of the formulation, though under some circumstances the effective concentration will be as little as 0.001% or as much as 2%, on the same basis.

The superior activity of the (1R,trans) esters of the invention is usefully employed when such an ester is present in n amount substantially greater than that usually present in the racemate of an oxyimino substituted ester. Therefore, use of the (1R,trans) esters of the invention in a form substantially free of other stereoisomers is preferred, for example in a (1R,trans) isomer purity of greater than about 85%, preferably in a (1R,trans) isomer purity greater than about 90% or even greater than 95%.

ILLUSTRATIVE EMBODIMENTS

The invention is illustrated by the following embodiments which describe the preparation and biological testing of typical species of the invention with respect to representative insects and acarines. The embodiments are presented for the purpose of illustration only and should not be regarded as limiting the invention in any way. The identity of the products, including intermediates, was confirmed by elemental, infrared and nuclear magnetic resonance spectral (NMR) analyses as necessary.

EMBODIMENT 1

(1R,trans)-2,2-dimethyl-3-((cyclopropylmethoxyimino)methyl)cyclopropanecarboxylic acid A solution of 1.4 g of (1R,trans)-caronaldehydic acid and 0.5 g each of cyclopropylmethoxyamine and cyclopropylmethoxyamine hydrochloride in 50 ml of water was stirred for about 8 hours at room temperature in the presence of 1.2 g of sodium bicarbonate. The resulting mixture was filtered through celite. The filtrate was acidified with aqueous acid, the resulting solution was extracted with methylene chloride. The combined extracts were washed with water, then with saturated sodium chloride solution, dried over magnesium sulfate and stripped to give 2.0 g of the desired product, mp 82°–85° C.

EMBODIMENT 2

αCyano-3-phenoxybenzyl (1R,trans)-2,2-dimethyl-3-((cyclopropylmethoxyimino)methyl)cyclopropanecarboxylate A mixture of 1.8 g of (1R,trans)-2,2-dimethyl-3-((cyclopropylmethoxyimino)methyl)cyclopropanecarboxylic acid, 2.30 g of α-cyano-3-phenoxybenzyl bromide, 0.05 g of tetrabutylammonium hydrogen sulfate, 0.05 g of benzyltriethylammonium chloride, 0.58 g of potassium carbonate, 10 ml of toluene and 6 ml of water was heated at 60°–70° for 4 hours, let stand overnight at room temperature and reheated at 60°–70° for an additional eight hours. The resulting reaction mixture separated into layers. The toluene layer was separated, washed with water, then with saturated sodium bicarbonate and saturated sodium chloride, dried over magnesium sulfate and stripped to give an oil. This oil was chromatographed on silica gel with a mixture of ether-pentane (1:4 ratio) as the eluant to give 2.7 g of desired product as a yellow oil, $[\alpha]_D^{25}$—16.2, (CHCl$_3$; c=0.02 g/cc).

Following procedures similar to Embodiment 2 above, α-cyano-3-phenoxybenzyl(1R,trans)-2,2-dimethyl-3-((neopentoxyimino)methyl)cyclopropanecarboxylate, α-cyano-3-phenoxybenzyl (1R,trans)-2,2-dimethyl-3-((n-pentoxyimino)methyl)cyclopropanecarboxylate, α-cyano-3-phenoxybenzyl (1R,trans)-2,2-dimethyl-3-((cyclopentoxyimino)methyl)cyclopropanecarboxylate, α-cyano-3-phenoxybenzyl (1R,trans)-2,2-dimethyl-3-((isopropoxyimino)methyl)cyclopropanecarboxylate, and α-cyano-3-phenoxybenzyl (1R,trans)-2,2-dimethyl- 3-((isopropoxyimino)methyl)cyclopropanecarboxylate are prepared.

The racemic form of the oxyimino-substituted cyclopropanecarboxylates wherein R represents a group of formula I, II, III, IV, V, VI or VII are also pesticidal. These esters and their acid intermediates are prepared by methods similar to those used in Examples 1 and 2 using racemic carbonaldehydic acid as a starting material to form the oxyimino-substituted acid moiety.

EMBODIMENT 3

Pesticidal Activity

Activity of the compounds of this invention with respect to insect and acarine pests determined by using test methods to test the toxicity of the compounds as follows:

I. Houseflies (*Musca domestica* (Linne)) were tested by placing 50 5- to 5-day old houseflies into a spray cage and spraying with 0.6 ml of a solution of test compound. After spraying, the flies were anesthetized with $CO_2$ and transferred to a recovery cage containing a milk pad for food. The cages were held for 18–20 hours after which mortality counts were made. Both dead and moribund were counted. The tests were conducted employing several different dosage rates of each test compound.

II. Pea aphids (*Acyrthosiphon pisum* (Harris)) were tested by placing about 100 aphids on broad bean plants. The plants were sprayed with dilutions of acetone solution of test compound into water containing an emulsifier and held in containers under laboratory conditions for 18 to 20 hours at which time the living aphids in the containers were counted. The tests were conducted employing several different dosage rates of each test compound.

III. Adult female two-spotted spider mites (*Tetranychus urticae* (Koch)) were tested by placing 50–75 mites on the bottom side of leaves of pinto bean plants. The leaves were sprayed with dilutions of acetone solution of test compound into water containing an emulsifier and kept under laboratory conditions for about 20 hours at which time mortality counts were made. The test were conducted employing several different dosage rates of test compounds.

IV. Mosquito larvae (*Anopheles albimanus* (Weide)) were tested by placing ten living and active mosquito larvae in a jar containing a 0.1 ml aliquot of a 1% acetone solution of test compound thoroughly mixed with 100 ml of distilled water. After 18–22 hours, mortality counts were taken. Both dead and moribund larvae were counted as dead. Larvae which did not swim after being prodded with a needle were considered moribund. The tests were conducted employing several different dosage rate for each test compound.

V. Corn earworm larvae (*Heliothis zea* (Boddie)) were tested by spraying a broad bean plant with dilutions of acetone solution of test compound into water containing an emulsifier. Immediately after spraying, 5 larvae were transferred to the plant and held for 44–46 hours, at which time the dead and moribund larvae were counted. The tests were conducted employing several different dosage rates for each test compound.

In each instance, the toxicity of the compound of the invention was compared to that of a standard pesticide (Parathion), its relative toxicity then being expressed in terms of the relationship between the amount of compound of the invention and the amount of the standard pesticide required to produce the same percentage (50) of mortality in the test insects or acarine. Assigning the standard pesticide an arbitrary rating of 100, the toxicities of the compounds of the invention were expressed in terms of the toxicity indexes, which compares the toxicity of the compounds of the invention with that of the standard pesticide. That is to say, a test compound having a Toxicity Index of 50 would be half as active, while one having a Toxicity Index of 200 would be twice as active as the standard pesticide.

Moreover, the (1R,trans) compounds of the invention have been found to be unexpectedly more active in the control of certain pests, particularly the corn earworm larvae and mites, than the corresponding structurally most similar (1R,trans) compounds specifically disclosed in U.S. Pat. No. 3,922,269. Examples of such esters of the 2,2-dimethyl-3-((oxyimino)methyl)cyclopropanecarboxylic acid are compared in Table 1 below, expressed in terms of Toxicity Index to parathion as a standard equal to 100.

Table 1.

| | | | | | | | |
|---|---|---|---|---|---|---|---|
| PESTICIDAL ACTIVITY OF α-CYANO-3-PHENOXYBENZYL 3,3-DIMETHYL-3-((OXYIMINO)METHYL)CYCLOPROPANECARBOXYLATES EXPRESSED AS TOXICITY INDEX RELATIVE TO THAT OF PARATHION AS A STANDARD EQUAL TO 100 | | | | | | | |
| R' | Configuration of Acid | E/Z Isomer Content | House Fly | Pea Aphid | Corn Earworm | 2-Spotted Mite | Mosquito Larvae |
| —CH₂—△ | 1R,trans[1] | E-Z mixture | 620 | 150 | 130 | 37 | 520 |
| —CH₃ | 1R,trans[2] | Z isomer | 35 | 24 | 12 | 0 | 23 |
| —CH₃ | 1R,trans[2] | E isomer | 73 | 28 | 27 | 0 | 96 |

[1]Embodiment 2
[2]Compound named in Example 5 of U.S. Pat. No. 3,922,269.
+ Toxcity Index means >0 but <1.

We claim:

1. A (1R,trans)-cyclopropanecarboxylate, substantially free of other stereoisomers, of the formula

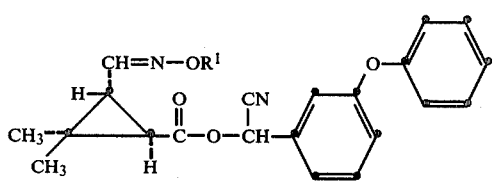

wherein R¹ is a (cycloalkyl)alkyl group containing from 3 to 6 carbon atoms and 4 to 8 total carbon atoms and the alcohol moiety is in the R,S-racemic or S-optical configuration.

2. α-Cyano-3-phenoxybenzyl (1R,trans)-2,2-dimethyl-3-((cyclopropylmethoxyimino)methyl)cyclopropanecarboxylate, substantially free of other stereoisomers, wherein the alcohol moiety is in the R,S-racemic or S-optical configuration.

3. A cyclopropanecarboxylate according to claim 2 wherein the alcohol moiety is in the S-optical configuration.

4. A pesticidal composition comprising a pesticidally effective amount of cyclopropanecarboxylate according to claim 2, and at least one agriculturally acceptable surface-active agent or carrier therefore.

5. A pesticidal composition comprising a pesticidally effective amount of an oxyimino-substituted (1R,trans)-cyclopropane compound according to claim 1 and at least one agriculturally acceptable surface-active agent or carrier therefore.

6. A method of controlling pests at a locus which comprises applying to the pests or to the locus a pesticidally effective amount of a cyclopropanecarboxylate according to claim 2.

7. A method of controlling pests at a locus which comprises applying to the pests or to the locus a pesticidally effective amount of an oxyimino-substituted (1R,trans)-cyclopropane carboxylate according to claim 1.

8. A method according to claim 7 wherein the pests are selected from the order Coleoptera, Lepidoptera, Diptera, Orthoptera, Hemiptera, Homoptera or Acarina.

9. A method according to claim 8 wherein in the pests are larvae of the order Lepidoptera.

10. A method according to claim 8 wherein the pests are of the order Acarina.

* * * * *

UNITED STATES PATENT AND TRADEMARK OFFICE
CERTIFICATE OF CORRECTION

PATENT NO. : 4,211,792

DATED : July 8, 1980

INVENTOR(S) : STEVEN A. ROMAN and SAMUEL B. SOLOWAY

It is certified that error appears in the above-identified patent and that said Letters Patent are hereby corrected as shown below:

Claim 1, line 5, after "6", insert -- ring --.

Signed and Sealed this

Seventh Day of October 1980

[SEAL]

Attest:

SIDNEY A. DIAMOND

Attesting Officer

Commissioner of Patents and Trademarks